United States Patent
Kulthe

(10) Patent No.: US 10,220,676 B2
(45) Date of Patent: Mar. 5, 2019

(54) AIR QUALITY ESTIMATION METHODS AND SYSTEMS

(71) Applicant: GM GLOBAL TECHNOLOGY OPERATIONS LLC, Detroit, MI (US)

(72) Inventor: Rulthe Ranjita Rajendrakumar Kulthe, Bangluru (IN)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 467 days.

(21) Appl. No.: 15/015,867

(22) Filed: Feb. 4, 2016

(65) Prior Publication Data
US 2017/0225537 A1    Aug. 10, 2017

(51) Int. Cl.
*B60H 1/00* (2006.01)
*G01K 13/02* (2006.01)
*G01N 33/00* (2006.01)
*G01P 5/00* (2006.01)

(52) U.S. Cl.
CPC .......... *B60H 1/008* (2013.01); *B60H 1/00821* (2013.01); *G01K 13/02* (2013.01); *G01N 33/0062* (2013.01); *G01P 5/00* (2013.01); *B60H 1/00771* (2013.01); *B60H 1/00849* (2013.01)

(58) Field of Classification Search
CPC .. B60H 1/008; B60H 1/0071; B60H 1/00821; B60H 1/00849; G01N 33/0062; G01P 5/00; G01K 13/02
USPC .......................................................... 454/75
See application file for complete search history.

(56) References Cited

U.S. PATENT DOCUMENTS

| | | | |
|---|---|---|---|
| 5,670,714 A * | 9/1997 | Sorensen ........... | B60H 1/00764 454/74 |
| 7,682,441 B2 * | 3/2010 | Drews-Nicolai ........ | C09D 7/62 106/442 |
| 8,509,991 B2 | 8/2013 | Bai | |
| 9,952,190 B2 * | 4/2018 | Cogill ................ | G01N 33/0075 |
| 2007/0243808 A1 * | 10/2007 | Mathur .............. | B60H 1/00764 454/75 |
| 2009/0192681 A1 * | 7/2009 | Hayashi ............. | B60G 17/0164 701/45 |

* cited by examiner

*Primary Examiner* — Gregory L Huson
*Assistant Examiner* — Dana K Tighe
(74) *Attorney, Agent, or Firm* — Lorenz & Kopf, LLP

(57) ABSTRACT

Systems and methods are provided for estimating a quality of air in proximity to a vehicle. In one embodiment, a method includes: determining a radius of the vehicle; estimating a number of vehicles within the radius of the vehicle; estimating the quality of air based on the number of vehicles; and selectively generating a control signal to an air inlet valve based on the quality of air.

16 Claims, 3 Drawing Sheets

AIR QUALITY ESTIMATION METHODS AND SYSTEMS

FIELD

The present disclosure generally relates to the field of vehicles and, more specifically, to methods and systems for estimating a quality of air based on vehicle traffic conditions.

BACKGROUND

Certain vehicles today may rely on sensor data received from one or more air quality sensors to determine air quality. The air quality sensors sense the quality of the ambient air in proximity to the vehicle and provide the vehicle with the sensed data. The vehicle interprets the sensed data to determine a quality of the air. The inclusion of such sensors in a vehicle may increase costs.

Accordingly, it is desirable to provide methods and systems for estimating air quality without the use of an air quality sensor. Furthermore, it is desirable to provide methods and systems for compensating when the determined air quality is poor. Furthermore, other desirable features and characteristics of the present invention will be apparent from the subsequent detailed description and the appended claims, taken in conjunction with the accompanying drawings and the foregoing technical field and background.

SUMMARY

Systems and methods are provided for estimating a quality of air in proximity to a vehicle. A method includes: determining a radius of the vehicle; estimating a number of vehicles within the radius of the vehicle; estimating the quality of air based on the number of vehicles; and selectively generating a control signal to an air inlet valve based on the quality of air.

A system includes a first module that estimates, by a processor, a number of vehicles within a radius of the vehicle. The system further includes a second module that estimates, by a processor, the quality of air based on the number of vehicles. The system further includes a third module that selectively generates, by a processor, a control signal to an air inlet valve based on the quality of air.

BRIEF DESCRIPTION OF THE DRAWINGS

The present disclosure will hereinafter be described in conjunction with the following drawing figures, wherein like numerals denote like elements.

DETAILED DESCRIPTION OF THE INVENTION

The following detailed description is merely exemplary in nature and is not intended to limit the invention or the application and uses of the invention. Furthermore, there is no intention to be bound by any theory presented in the preceding background or the following detailed description. As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Figure 1:
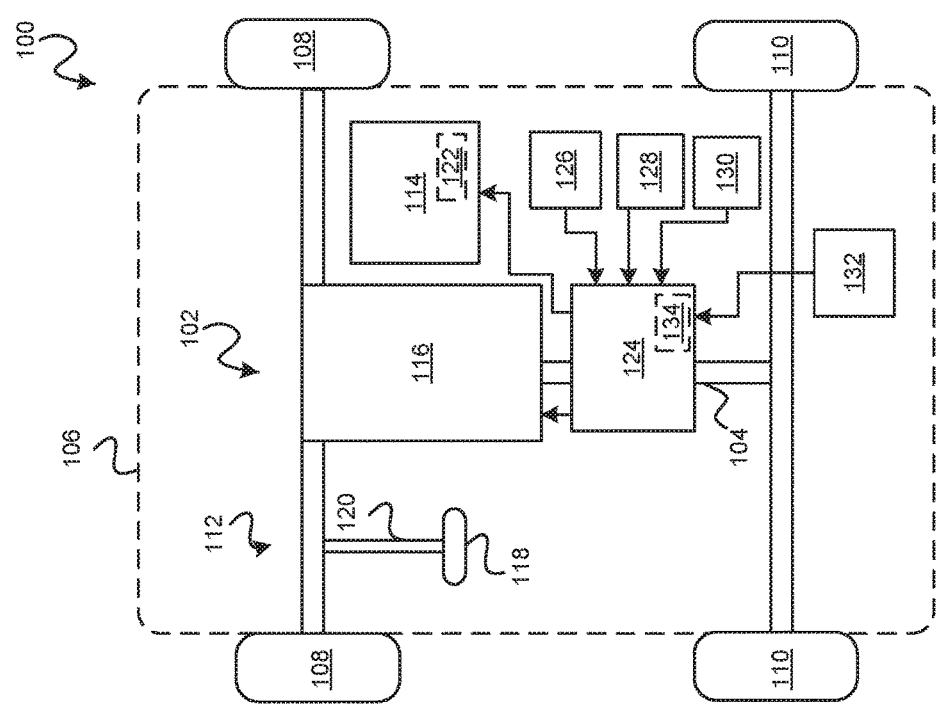
FIG. 1 is a functional block diagram illustrating a vehicle having an air quality estimation and control system in accordance with various embodiments.

With reference to FIG. 1, a vehicle 100 is shown that includes an air quality estimation and control system 102 in accordance with various embodiments. Although the figures shown herein depict an example with certain arrangements of elements, additional intervening elements, devices, features, or components may be present in an actual embodiment. It should also be understood that FIG. 1 is merely illustrative and may not be drawn to scale.

As depicted in FIG. 1, the vehicle 100 generally includes a chassis 104, a body 106, front wheels 108, rear wheels 110, a steering system 112, a heating ventilation and/or air conditioning (HVAC) system 114, and a propulsion system 116. In various embodiments, the body 106 is arranged on the chassis 104 and substantially encloses the other components of the vehicle 100. The body 106 and the chassis 104 may jointly form a frame. The wheels 108-110 are each rotationally coupled to the chassis 104 near a respective corner of the body 106. The steering system 112, at a minimum, includes a steering wheel 118 coupled to a steering shaft 120. In various embodiments, the steering system 112 further includes various other features (not depicted in FIG. 1), such as a steering gear, intermediate connecting shafts between the column and the gear, connection joints, either flexible or rigid, allowing desired articulation angles between the intermediate connecting shafts, and tie-rods. The steering gear, in turn, comprises a rack, input shaft, and internal gearing. The steering system 112 influences the steerable front road wheels 108 during steering based upon any torque received from a driver of the vehicle 100 via the steering wheel 118.

The HVAC system 114 includes one or more components to control the in-vehicle air temperature and air quality. In various embodiments, the HVAC system 114 includes, amongst other features, an air inlet flap 122 that permits ambient air to flow from outside the vehicle 100 to inside of the vehicle 100. The air inlet flap 122 may be mechanically and/or electronically controlled by one or more actuator devices (not shown).

The propulsion system 116 may include any one of, or combination of, a number of different types of propulsion systems, such as, for example, a gasoline or diesel fueled combustion engine, a "flex fuel vehicle" (FFV) engine (i.e., using a mixture of gasoline and ethanol), a gaseous compound (e.g., hydrogen or natural gas) fueled engine, a combustion/electric motor hybrid engine, and an electric motor. As can be appreciated, the vehicle 100 may be any one of a number of different types of automobiles, such as, for example, but not limited to, a sedan, a wagon, a truck, or a sport utility vehicle (SUV), and may be two-wheel drive (2WD) (i.e., rear-wheel drive or front-wheel drive), four-wheel drive (4WD) or all-wheel drive (AWD), or any other type of vehicle.

The vehicle 100 further includes at least one controller 124 that is communicatively coupled to one or more sensors 126-130 and a global positioning system (GPS) 132. In various embodiments, the sensors 126-130 include, but are not limited to, an ambient air temperature sensor 126, a wind speed sensor 128, and a vehicle speed sensor 130. The ambient air temperature sensor 126 senses a temperature of the ambient air outside of the vehicle 100 and generates temperature sensor signals based thereon. The wind speed sensor 128 senses a speed of the air or wind outside of the vehicle 100 and generates wind speed sensor signals based thereon. The vehicle speed sensor 130 senses a rotational speed of the one or more wheels 108-110 of the vehicle 100 and generates vehicle speed sensor signals based thereon. The GPS 132 includes one or more communication devices for communicating with one or more satellites. The GPS 132 provides time and location information to the controller 124 based on the communications with the satellites.

The controller 124 receives and processes the various sensor signals and the GPS information and controls one or more components of the vehicle 100 based thereon. In various embodiments, the controller 124 controls the HVAC system 114. As can be appreciated, the controller 124 may control other vehicle components such as, but not limited to, the steering system 112, the propulsion system 116, and/or other components not described.

In various embodiments, the controller 124 includes an air quality estimation and control module 134. The air quality estimation and control module 134 receives the sensor signals and the GPS information. The air quality estimation and control module 134 processes the sensor signals and the GPS information to estimate a quality of the air outside of the vehicle 100. The air quality estimation and control module 134 generates control signals to control the HVAC system 122 based on the estimated air quality. For example, if the estimated air quality is poor, then the air quality estimation and control module 134 generates control signals to control the inlet flap 122 of the HVAC system 114 such that intrusion of the pollutants into the vehicle 100 is prevented. For example, the control signals control one or more actuator devices associated with the inlet flap 122 to control a position of the inlet flap 122.

Figure 2:
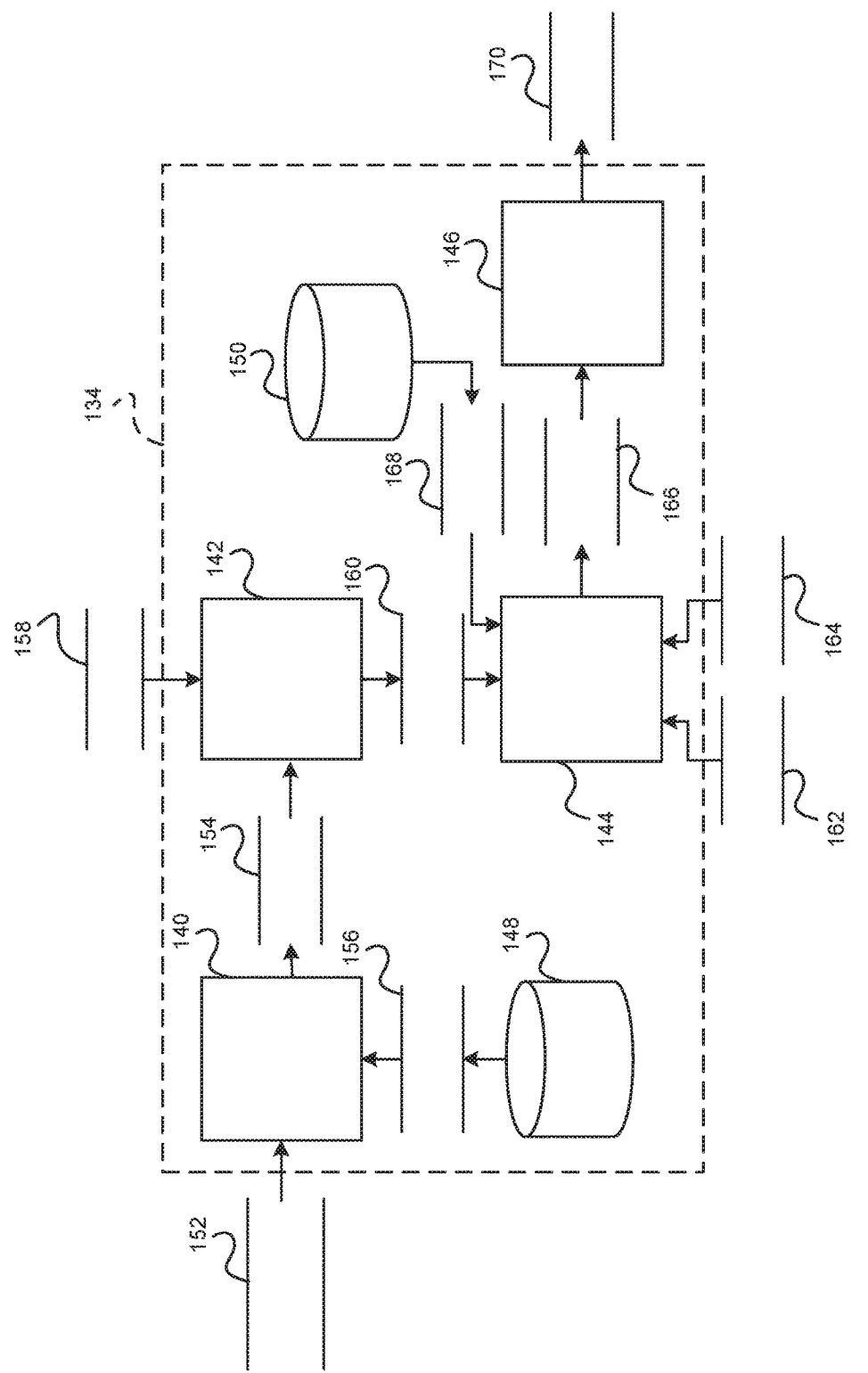
FIG. 2 is a dataflow diagram illustrating an air quality estimation and control module in accordance with various embodiments.

Referring now to FIG. 2 and with continued reference to FIG. 1, a dataflow diagram illustrates the air quality estimation and control module 134 of FIG. 1 in accordance with various embodiments. As can be appreciated, various embodiments of the air quality estimation and control module 134, according to the present disclosure, may include any number of sub-modules. For example, the sub-modules shown in FIG. 2 may be combined and/or further partitioned to similarly estimate air quality and control one or more features of the HVAC system 122. As discussed above, inputs to the air quality estimation and control module 134 may be received from the sensors 126-130 of the vehicle 100 and/or other sensors (not shown), received from other controllers (not shown) of the vehicle 100, received from other modules of the controller 124, or determined by other sub-modules (not shown) of the air quality estimation and control module 134. In various embodiments, the air quality estimation and control module 134 includes a radius determination module 140, a vehicle number determination module 142, an air quality estimation module 144, a recirculation control module 146, a radius datastore 148, and an air quality datastore 150.

The radius determination module 140 receives as input ambient air temperature data 152. The ambient air temperature data 152 may be based on, for example, the sensor signals received from the ambient air temperature sensor 126. The radius determination module 140 determines a radius 154 based on the ambient air temperature data 152. The radius 154 corresponds to a radius around the vehicle 100 (e.g., where the vehicle is the center of the radius). For example, the radius 154 may be determined from a value 156 that is determined from a lookup table stored in the radius datastore 148.

The lookup table may be a one dimensional interpolation table that is indexed by ambient air temperature. The radius values can be populated in the lookup table based on relationships between ambient air temperature, air density, and smoke travel characteristics. For example, if ambient air temperature is low, the air density will be higher. A higher air density will not allow smoke to settle on the ground. Higher smoke temperature and lower pressure will cause smoke to flow upwards. In this case there is less probability that the smoke will travel a long distance to reach the vehicle 100. Thus, at low ambient air temperatures, the radius to evaluate around the vehicle 100 may be set to a smaller value (e.g., Radius=200 m for ambient air temperature=5 degrees and less, 500 m for ambient air temperature=6 degrees to 20 degrees, etc.]); and at higher ambient air temperatures, the radius to evaluate around the vehicle may be set to a greater value (e.g., 1 Km for ambient air temperature=21 degrees or more).

The vehicle number determination module 142 receives as input the determined radius 154 and GPS data 158. The GPS data 158 may include coordinates of other vehicles within a proximity of the vehicle 100. The GPS data 158 may be based on, for example, the information received from the GPS 132. The vehicle number determination module 142 determines a number of vehicles 160 within the determined radius 154 of the vehicle 100 based on the GPS data 158. For example, the vehicle number determination module 142 keeps a count of the number of other vehicles having coordinates within the determined radius of the vehicle 100 as identified in the GPS data 158; and the count is set equal to the number of vehicles 160.

The air quality estimation module 144 receives as input the number of vehicles 160, wind speed data 162, and vehicle speed data 164. The wind speed data 162 may be based on, for example, the sensor signals received from the wind speed sensor 128. The vehicle speed data 164 may be based on, for example, the sensor signals received from the vehicle speed sensor 130. The air quality estimation module 144 estimates a quality of air 166 in proximity to the vehicle 100 based on the received data 160-164. For example, the estimated air quality 166 may be determined from a value 168 that is determined from a lookup table stored in the air quality datastore 150.

The lookup table may be a one dimensional interpolation table that is indexed by the number of vehicles 160. For example, the air quality values 168 can be populated in the lookup table based on a predetermined emission value per vehicle. In another example, the air quality values 168 can indicate low, medium, or high and can be based on a range of vehicles (e.g., number of vehicles 160<5, then the quality of air 166 is set to no pollution; number of vehicles 160=5-15, then the quality of air 166 is set to low pollution; number of vehicles 160>15, then the quality of air 166 is set to high pollution). As can be appreciated, in various embodiments, information about the other vehicles (e.g., make, model, year, etc.) may also be used to determine the air quality values 168 if it is available from the GPS 132 or other system.

The recirculation control module 146 receives as input the estimated air quality 166. The recirculation control module 1446 evaluates the estimated air quality 166 and selectively generates controls signals 170 to control the HVAC system 114 based on the evaluation. For example, the recirculation control module 146 generates control signals 170 to control the inlet flap 122 to a position that prevents airflow into the vehicle 100 when the air quality estimation is greater than a first threshold. In another example, the recirculation control module 146 generates control signals 170 to control the inlet flap 122 to a second position to permit airflow into the vehicle 100 when the air quality estimation is less than a second threshold. As can be appreciated, the first threshold and the second threshold may be the same or different values.

Figure 3:
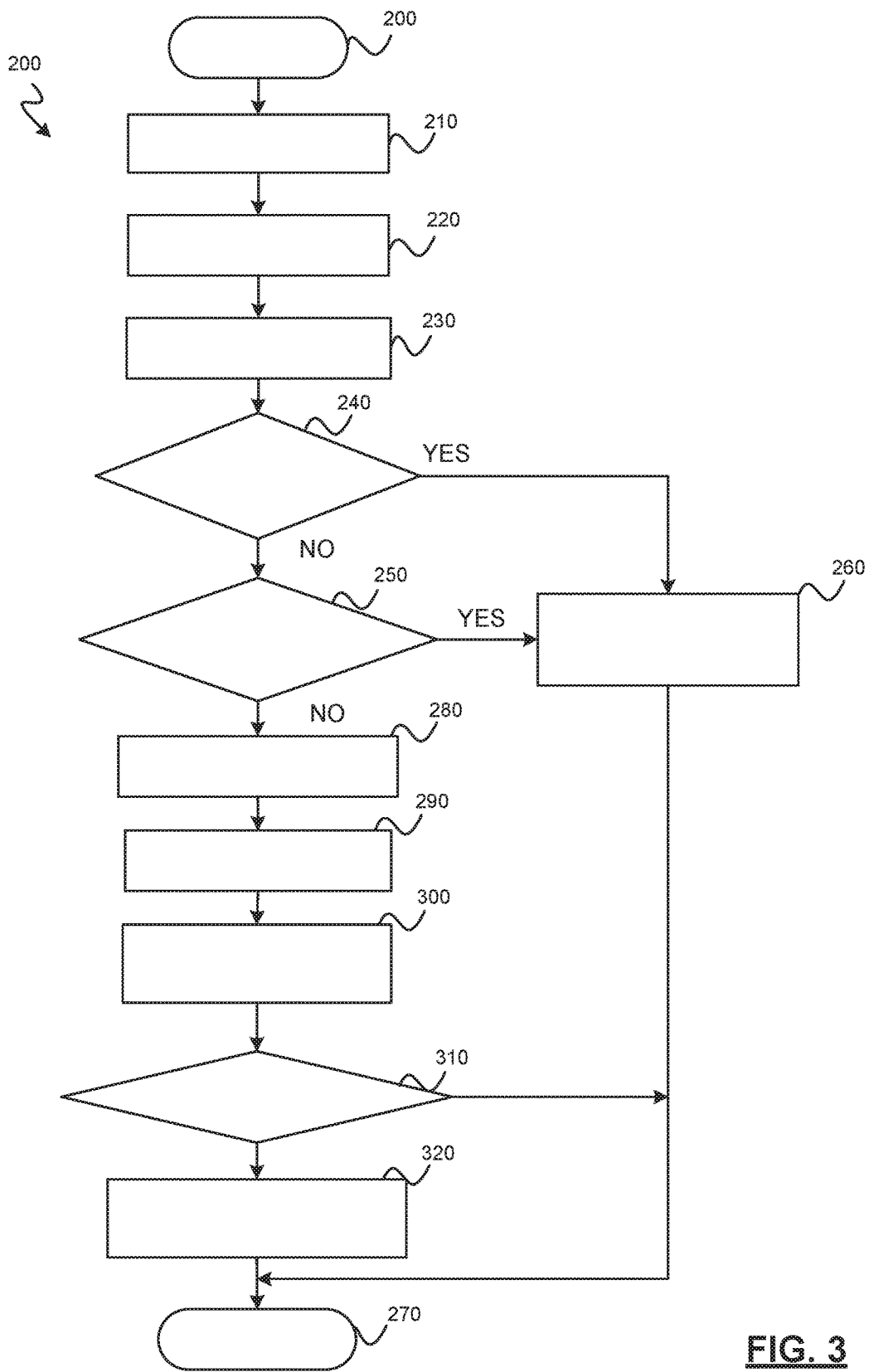
FIG. 3 is a flowchart illustrating an air quality estimation and control method in accordance with various embodiments.

With reference now to FIG. 3, a flowchart of a method 200 for estimating a quality of air in proximity to the vehicle and controlling the HVAC system based thereon is shown in accordance with exemplary embodiments. The method 200 can be utilized in connection with the vehicle 100 and the air quality estimation and control system 102, in accordance with exemplary embodiments. As can be appreciated in light of the disclosure, the order of operation within the method is not limited to the sequential execution as illustrated in FIG. 3, but may be performed in one or more varying orders as applicable and in accordance with the present disclosure.

As depicted in FIG. 3, the method may begin at 205. The ambient air temperature sensor signals are received and processed to determine the ambient air temperature data 152 at 210. The wind speed sensor signals are received and processed to determine the wind speed sensor data 162 at 220. The vehicle speed sensor signals are processed to determine the vehicle speed data 164 at 230. The wind speed sensor data 162 and the vehicle speed sensor data 164 is evaluated at 240 and 250. For example, it is determined whether the wind speed is greater than a wind speed pollution threshold at 240, and whether the vehicle speed is greater than a vehicle speed pollution threshold at 250. If the wind speed is greater than the wind speed threshold at 240, or the vehicle speed is less than the vehicle speed pollution threshold at 250, it is determined that there is no effective air pollution at 260 and the method may end at 270.

If, however, the wind speed is less than the wind speed pollution threshold at 240 and the vehicle speed is less than the vehicle speed pollution threshold at 250, the method continues with estimating the quality of air 166 outside of the vehicle 100 and optionally, controlling the HVAC system 114 of the vehicle 100 based thereon at 280-300. For example, the radius 154 is determined based on the ambient air temperature data 152 at 280. The number of vehicles 160 within the determined radius 154 is determined based on the GPS data 158 at 290. The air quality 166 is estimated based on the number of vehicles 160 at 300.

Optionally, the estimated air quality is evaluated at 310. For example, if the estimated air quality 166 is greater than a threshold at 310, the control signals 170 are generated to control the inlet flap 122 to prevent air from entering the vehicle at 320. Otherwise, the method may end at 270.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for estimating a quality of air in proximity to a vehicle, comprising:
   determining a radius of the vehicle;
   estimating, by a processor, a number of vehicles within the radius of the vehicle;
   estimating, by a processor, the quality of air based on a lookup table indexed by the number of vehicles when at least one of wind speed and vehicle speed is below a threshold; and
   selectively generating a control signal to an air inlet valve based on the quality of air.

2. The method of claim 1, wherein the determining the radius comprises determining the radius based on ambient air temperature.

3. The method of claim 1, wherein the estimating the quality of air comprises estimating a quality to be at least one of no pollution, low pollution, and high pollution.

4. The method of claim 1, wherein the estimating the quality of air is based on the wind speed.

5. The method of claim 4, wherein the estimating the quality of air comprises estimating the quality of air to indicate substantially no pollution when the wind speed is above a threshold.

6. The method of claim 1, wherein the estimating the quality of air is based on the vehicle speed.

7. The method of claim 6, wherein the estimating the quality of air comprises estimating the quality of air to indicate substantially no pollution when the vehicle speed is above a threshold.

8. The method of claim 1, wherein the selectively generating comprises generating the control signal to prevent airflow into the vehicle when the quality of air is above a threshold.

9. A system for estimating a quality of air in proximity to a vehicle, comprising:
   a first module that estimates, by a processor, a number of vehicles within a radius of the vehicle;
   a second module that estimates, by a processor, the quality of air based on a lookup table indexed by the number of vehicles when at least one of wind speed and vehicle speed is below a threshold; and
   a third module that selectively generates, by a processor, a control signal to an air inlet valve based on the quality of air.

10. The system of claim 9, further comprising a fourth module that determines, by a processor, the radius based on ambient air temperature.

11. The system of claim 9, wherein the second module estimates the quality of air to be at least one of no pollution, low pollution, and high pollution.

12. The system of claim 9, wherein the second module estimates the quality of air based on the wind speed.

13. The system of claim 12, wherein the second module estimates the quality of air to indicate substantially no pollution when the wind speed is above a threshold.

14. The system of claim 9, wherein the second module estimates the quality of air based on the vehicle speed.

15. The system of claim 14, wherein the second module estimates the quality of air to indicate substantially no pollution when the vehicle speed is above a threshold.

16. The system of claim 9, wherein the third module generates the control signal to prevent airflow into the vehicle when the quality of air is above a threshold.

\* \* \* \* \*